United States Patent [19]

Demassey et al.

[11] Patent Number: 5,401,771
[45] Date of Patent: Mar. 28, 1995

[54] METHOD OF COMBATTING HOUSEHOLD INSECTS

[75] Inventors: Jacques Demassey, Montevrain; Jean-Pierre Demoute, Neuilly Plaisance; Pierre Pastre, Marseille Cedex; André Teche, Neuville les Dieppe, all of France

[73] Assignee: Roussel-Uclaf, France

[21] Appl. No.: 82,761

[22] Filed: Jun. 25, 1993

[30] Foreign Application Priority Data

Jul. 1, 1992 [FR] France ................... 92 08083

[51] Int. Cl.$^6$ .................. A01N 37/08; A01N 37/34
[52] U.S. Cl. ................................................ 514/521
[58] Field of Search ...................... 514/531, 521

[56] References Cited

FOREIGN PATENT DOCUMENTS 0050534 4/1982 France .

Primary Examiner—Allen J. Robinson
Assistant Examiner—Brian C. Bembenick
Attorney, Agent, or Firm—Bierman and Muserlian

[57] ABSTRACT

An insecticidal composition comprising an insecticidally effective amount of (S) α-cyano-3-phenoxy-benzyl(1R, trans) 2,2-dimethyl-3-[(ΔZ) 2-fluoro-3-oxo-3-methoxy-propenyl]-cyclopropane carboxylate and an inert carrier having excellent insecticidal activity and low mammal toxicity.

4 Claims, No Drawings

METHOD OF COMBATTING HOUSEHOLD INSECTS

STATE OF THE ART (S) α-cyano-3-phenoxy-benzyl(1R, trans) 2,2-dimethyl-3-[(ΔZ) 2-fluoro-3-oxo-3-methoxy-propenyl]-cyclopropane carboxylate (compound A) is described in European patent application No. 50,534 which describes a large family of compounds having pesticidal properties. Also described therein are the stereoisomers 1R, trans ΔE (product B), 1R, cis ΔE (product C) and 1R, cis ΔZ (product D). No particular use of product A is described in this patent application. Up to now, only one product of the nor-pyrethric family has been available commercially: it is acrinathrin, a product of 1R, cis ΔZ structure endowed with acaricide properties.

Several publications have been devoted to the family of products to which product A belongs: the nor-pyrethric series. For example, J. Tessier published in 1 'Actualité Chimique of December 1986, p.12: "These halogenated nor-pyrethric structures in the terminal position offer a maximum insecticide activity when the spatial arrangement of the chain is the same as for the real norpyrethric esters, but taking into account the halogen modifies the designation to (1R)-cis-E.

OBJECTS OF THE INVENTION

It is an object of the invention to provide novel insecticidal compositions with a high insecticidal activity and a low toxicity to mammals and a novel method of combatting insects.

This and other objects and advantages of the invention will become obvious from the following detailed description.

THE INVENTION

The novel insecticidal compositions of the invention with a low mammal toxicity are comprised of an insecticidally effective amount of (S) α-cyano-3-phenoxy-benzyl(1R, trans) 2,2-dimethyl-3-[(ΔZ) 2-fluoro-3-oxo-3-methoxy-propenyl]-cyclopropane carboxylate and an inert carrier.

Referring to compounds of the formula

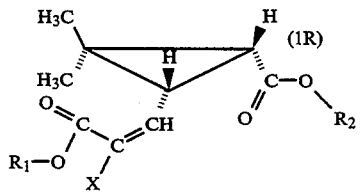

In the general formula of new diesters, three parameters are available: —$R_2$ corresponds to the conventional pyrethrinoid alcohols (there are a good fifteen or so of them), —$R_1$ offers a much wider range of possibilities, because this alkyl can be linear or branched, cyclic or non cyclic, optionally unsaturated or substituted by heteroatoms and finally, X is hydrogen, halogen or more generally, an attractive group.

By using the three parameters, an almost infinite number of variations is available which allows the biological properties of the diesters to be adjusted, by strengthening for example the activity against certain targets up to now not very sensitive to pyrethrinoids (acaridae, for example), or by having a greater effect on certain arthropod families than others.

One skilled in the art looking for a new insecticide in the nor-pyrethric or halo nor-pyrethric series was led to use the 1R, cis series and to exclude the 1R,trans products. It has just been discovered that one of the nor-pyrethric esters of 1R,trans structure, namely product A, has remarkable properties as is shown by the following biological tests:

Product A has an $$\frac{\text{insecticide activity}}{\text{toxicity for mammals}}$$

ratio which is greater than those of products B, C and D. Product A is as active as the best of the products while being much less toxic to mammals. Product A can therefore be used as an insecticide in the household or at the exterior for man and animals, as well as in places where grains and other products intended for human and animal foodstuffs are stored.

Product A therefore conforms to the current ecological criteria for the use of pesticides, as indicated for example by Jean Tessier in the annals of the 1986 PARASITIS congress.

"1—It is preferable to use the isomer with maximum effectiveness, rather than a mixture; in this way, one avoids diluting the activity by constituents with a weak insecticide value, but whose presence in the environment may prove to be undesirable in the long-term.

2—Chemical synthesis reactions, which are costly in terms of energy, solvents and reagents, must be used, as far as possible, to produce the most effective structure and no other. As we approach the end of the twentieth century, obtaining inactive isomers constitutes an anachronism and, from an economic point of view, a real squandering.

To sum up, it is reassuring that users benefit from products of increased effectiveness, through improved isomeric purity. This is the result of taking into account stereochemical factors in order to produce maximum activity. Moreover, this approach is commonplace for many classes of medicaments."

The compositions of the invention are quite particularly intended for public and private hygiene and for the protection of the environment. The compositions can be in different forms, for example in the form of sprays, aerosols, ready-to-use emulsifiable concentrates, baits and fumigants.

In addition to the active ingredient, the compositions of the invention may contain one or more other active ingredients such as, a synergist, a stabilizing agent, a perfume or a coloring agent.

A preferred insecticide composition is characterized in that it is in the form of a spray, as well as the insecticide compositions characterized in that they are presented in the form of an aerosol. Preferably, the compositions contain 0.05 to 4% by weight of Product A.

In the following examples, there are described several preferred embodiments to illustrate the invention. However, it is to be understood that the invention is not intended to be limited to the specific embodiments.

EXAMPLE 1

A spray was prepared comprising 99.9 of deodorized petroleum and 0.1 g of (S) α-cyano-3-phenoxy-benzyl (1R, trans) 2,2-dimethyl-3-[(ΔZ) 2-fluoro-3-oxo-3-methoxy-propenyl]-cyclopropane carboxylate (product A).

EXAMPLE 2

An aerosol was prepared comprising 0.1 g of Product A, 29.90 g of deodorized petroleum and 70.0 g of propellant.

EXAMPLE 3

An emulsifiable concentrate was prepared comprising of 2 g of Product A, 0.1 g of BHT (2-6-ditert-butyl-4-methyl-phenol), 0.01 g of acetic acid, 4 g of calcium dodecyl benzene sulfonate, 4 g of polyoxyethylenated ricin oil and 89.89 g of Solvesso 100 ®.

Biological Activity

A. Study of the killing effect on the housefly.

The insects used were 4-day old female houseflies and the operation was carried out by direct spraying at a concentration of 0.25 g/l in a Kearns and March chamber. The tested product was dissolved in Isopar L (petroleum solvent) with 5% acetone. 2 ml of solution were sprayed per second and 50 insects were used per treatment Checks were carried out every minute for 10 minutes, then after 15 minutes. The ($KT_{50}$) time in minutes where 50% of the insects were killed was determined and the results are in Table I.

TABLE I

| PRODUCTS | $KT_{50}$ IN KIN | DOSE IN g/l |
|---|---|---|
| A trans Z | 2.7 | 0.25 |
| C cis E | 2.7 | 0.25 |
| D cis Z | 3.7 | 0.25 |
| Bioallethrin | 10 | 0.25 |

B. Study of the knock-down effect on cockroaches

The test was carried out on 12-week old male cockroaches (Blattella germanica) and the operation was carried out by direct spraying in a 13.5 cm diameter glass chamber. The product tested was dissolved in Isopar and 0.75 ml of solution was sprayed for 2.5 seconds on 20 cockroaches having been placed beforehand in the chamber. The KD (percentage of cockroaches knocked down) after 5 minutes at a dose of 500 mg/l was determined and the products corresponding to 100% of KD insects at this does were evaluated at a dose of 100 mg/l by the same protocol and the results are in Table II.

TABLE II

| TETRAMETHRIN | 70% KILLED | AT 500 mg/l |
|---|---|---|
| A trans Z | 100% KILLED | at 100 mg/l |
| B trans E | 47% KILLED | at 100 mg/l |
| C cis E | 95% KILLED | at 100 mg/l |
| D cis Z | 90% KILLED | at 500 mg/l |

C. Acute toxicity on mammals
by oral route
    type: rats, vehicle: corn oil.
by intravenous route
    type: rats, vehicle: PEG 300.

The results were expressed in $LD_{50}$ mg/kg and the results obtained are as follows:

| PRODUCTS | O.R. | I.R. |
|---|---|---|
| A trans Z | $LD_{50} >> 2000$ | approx. 10 |
| B trans E | >200 | $2.5 < X < 5$ |
| C cis E | approx. 100 | $0.1 < X < 0.5$ |
| D cis Z | >200 | $2.5 < X < 7.5$ |

Conclusion

Product A (trans Z) has a good killing activity on cockroaches and on flies [equivalent notably to C (cis E)] but relative to the latter, it has a much weaker toxicity on mammals, at least 20 times lower both orally and by intravenously.

Various modifications of the compositions and method of the invention may be made without departing from the spirit or scope thereof and it should be understood that the invention is intended to be limited as defined in the appended claims.

What is claimed:

1. A method of combatting-household insects comprising contacting the insects with an insecticidally effective amount of (S) α-cyano-3-phenoxy-benzyl(1R, trans) 2,2-dimethyl-3-[(ΔZ) 2-fluoro-3-oxo-3-methoxy-propenyl]-cyclopropane carboxylate.

2. A composition of claim 1 in liquid spray from.

3. A composition of claim 1 in aerosol form.

4. A composition of claim 1 containing 0.05 to 4% by weight of the insecticidal ester.

\* \* \* \* \*